US012310934B2

(12) United States Patent
Sirota et al.

(10) Patent No.: US 12,310,934 B2
(45) Date of Patent: May 27, 2025

(54) METHODS OF TREATMENT OF SPONTANEOUS PRETERM BIRTH

(71) Applicants: The Regents of the University of California, Oakland, CA (US); The Leland Stanford Junior University, Stanford, CA (US)

(72) Inventors: Marina Sirota, Belmont, CA (US); Brian Le, San Jose, CA (US); Ronald Wong, San Carlos, CA (US); David Stevenson, Stanford, CA (US)

(73) Assignees: THE REGENTS OF THE UNIVERSITY OF CALIFORNIA, Oakland, CA (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 804 days.

(21) Appl. No.: 17/440,178

(22) PCT Filed: Mar. 20, 2020

(86) PCT No.: PCT/US2020/023865
§ 371 (c)(1),
(2) Date: Sep. 16, 2021

(87) PCT Pub. No.: WO2020/191297
PCT Pub. Date: Sep. 24, 2020

(65) Prior Publication Data
US 2022/0347135 A1 Nov. 3, 2022

Related U.S. Application Data

(60) Provisional application No. 62/975,196, filed on Feb. 11, 2020, provisional application No. 62/821,408, filed on Mar. 20, 2019.

(51) Int. Cl.
| | | |
|---|---|---|
| *A61K 31/192* | (2006.01) | |
| *A61K 31/135* | (2006.01) | |
| *A61K 31/167* | (2006.01) | |
| *A61K 31/19* | (2006.01) | |
| *A61K 31/222* | (2006.01) | |
| *A61K 31/353* | (2006.01) | |
| *A61K 31/4035* | (2006.01) | |
| *A61K 31/43* | (2006.01) | |
| *A61K 31/438* | (2006.01) | |
| *A61K 31/4402* | (2006.01) | |
| *A61K 31/4439* | (2006.01) | |
| *A61K 31/546* | (2006.01) | |
| *A61K 31/573* | (2006.01) | |
| *A61P 15/06* | (2006.01) | |

(52) U.S. Cl.
CPC .......... *A61K 31/192* (2013.01); *A61K 31/135* (2013.01); *A61K 31/167* (2013.01); *A61K 31/19* (2013.01); *A61K 31/222* (2013.01); *A61K 31/353* (2013.01); *A61K 31/4035* (2013.01); *A61K 31/43* (2013.01); *A61K 31/438* (2013.01); *A61K 31/4402* (2013.01); *A61K 31/4439* (2013.01); *A61K 31/546* (2013.01); *A61K 31/573* (2013.01); *A61P 15/06* (2018.01)

(58) Field of Classification Search
CPC ................................................... A61K 31/192
See application file for complete search history.

(56) References Cited

U.S. PATENT DOCUMENTS 7,884,093 B2  2/2011  Creasy et al.
8,828,981 B2 *  9/2014  Creasy .................. A61K 45/06
                                                604/522

OTHER PUBLICATIONS

Vora, et al. Meta-Analysis of Maternal and Fetal Transcriptomic Data Elucidates the Role of Adaptive and Innate Immunity in Preterm Birth. Front Immunol. 2018;9:993 (Published May 9, 2018).
Boyle et al., 'Repurposing simvastatin as a therapy for preterm labor: evidence from preclinical models', The FASEB Journal, vol. 33, pp. 2743-2758 (published Feb. 2019).
Bezold et al., 'The genomics of preterm birth: from animal models to human studies', Genome medicine, 2013, vol. 5, article No. 34, pp. 1-11 abstract (Published Apr. 29, 2013).
Bi et al., 'Repurposing of Proton Pump Inhibitors as first identified small molecule inhibitors of endo-B-N-acetylglucosaminidase (ENGase) for the treatment of NGLY1 deficiency, a rare genetic disease', Bioorganic & medicinal chemistry letters, 2017, vol. 27, pp. 2962-2966 abstract (Published Jul. 1, 2018).
Grenier et al., 'Computational drug repurposing for inflammatory bowel disease using genetic information', Computational and structural biotechnology journal, epub 07 , vol. 17, pp. 127-135 abstract (published Jan. 2019).
Chen et al., "Computational Discovery of Niclosamide Ethanolamine, a Repurposed Drug Candidate That Reduces Growth of Hepatocellular Carcinoma Cells In Vitro and in Mice by Inhibiting Cell Division Cycle 37 Signaling," Gastroenterology, 152(8):2022-2036 (2017).
Chen et al., "Reversal of cancer gene expression correlates with drug efficacy and reveals therapeutic targets," Nature Communications, 8:16022, 12 pages (2017).
Czeizel et al., "Possible association of folic acid supplementation during pregnancy with reduction of preterm birth: a population-based study," Eur J Obstet Gynecol Reprod Biol, 148(2):135-140 (2010).

(Continued)

*Primary Examiner* — Golam M Shameem
(74) *Attorney, Agent, or Firm* — MARSHALL, GERSTEIN & BORUN LLP

(57) ABSTRACT

Spontaneous preterm birth (sPTB) is premature delivery prior to 37 weeks of pregnancy and is a leading cause of infant mortality worldwide. sPTB is associated with a unique gene expression profile. Identified herein are numerous safe and proven therapeutic compositions used for unrelated indications that have the biological effect of reversing, in part, the gene expression profile of sPTB and which can be used in preventative or interventional treatments to prevent, delay, or ameliorate sPTB. The repurposed drugs include several Class A and Class B therapeutics that are regarded as safe or low risk in pregnant subjects.

12 Claims, 3 Drawing Sheets

(56) References Cited

OTHER PUBLICATIONS

Czeizel et al., "Preterm birth reduction after clotrimazole treatment during pregnancy," Eur J Obstet Gynecol Reprod Biol, 116(2):157-163 (2004).
Dudley et al, "Computational Repositioning of the Anticonvulsant Topiramate for Inflammatory Bowel Disease," Science Translational Medicine, 3(96):96ra76 (2011).
Fonseca et al., "Progesterone and the risk of preterm birth among women with a short cervix," N Engl J Med., 357(5):462-469 (2007).
Heng et al., "Whole blood gene expression profile associated with spontaneous preterm birth in women with threatened preterm labor," PLoS One, 9(5):1-13 (2014).
International Preliminary Report on Patentability from International Application No. PCT/US20/23865 dated Sep. 16, 2021.
International Search Report and Written Opinion from International Application No. PCT/US2020/023865 dated Jul. 8, 2020.
Lamb et al., "The Connectivity Map: using gene-expression signatures to connect small molecules, genes and disease," Science 313(5795): 1929-1935 (2006).
Le et al., "Computational discovery of therapeutic candidates for preventing preterm birth," JCI insight, 13(5), abstract, Tables 1-2 (2020).
Sirota et al., "Discovery and Preclinical Validation of Drug Indications Using Compendia of Public Gene Expression Data," Science Translational Medicine 3(96):96ra77 (2011).
Subramanian et al., "A Next Generation Connectivity Map: L1000 platform and the first 1,000,000 profiles," Cell 171(6):1437-1452.e17 (2017).
Vanky et al., "On the potential of metformin to prevent preterm delivery in women with polycystic ovary syndrome—an epi-analysis," Acta Obstetricia et Gynecologica Scandinavica, 91(12):1460-1464 (2012).

* cited by examiner

METHODS OF TREATMENT OF SPONTANEOUS PRETERM BIRTH

CROSS-REFERENCE TO RELATED APPLICATIONS

This application is a 35 USC § 371 national stage application of PCT/US2020/023865, entitled "Methods of Treatment of Spontaneous Preterm Birth," filed Mar. 20, 2020, which claims the benefit of priority to U.S. Provisional Patent Application Ser. No. 62/821,408 entitled "Methods of Treatment of Spontaneous Preterm Birth," filed Mar. 20, 2019, and to U.S. Provisional Patent Application Ser. No. 62/975,196 entitled "Methods of Treatment of Spontaneous Preterm Birth," filed Feb. 11, 2020, the contents of which prior applications are hereby incorporated by reference.

STATEMENT REGARDING FEDERALLY SPONSORED RESEARCH OR DEVELOPMENT

Not Applicable.

BACKGROUND OF THE INVENTION

Preterm birth (PTB) or birth before 37 weeks of gestation is the leading cause of infant mortality worldwide. According to global estimates in 2015, complications arising from PTB were responsible for 35.5% of neonatal deaths (and 17.8% of deaths in children under 5). Estimated rates of PTB vary by country with rates as low as 5% and as high as 18%, with a worldwide estimate of 11.1%. Even in non-fatal cases, prematurely-born children are at a higher risk for life-long neurodevelopmental sequelae, such as motor and cognitive impairments. Approximately two-thirds of PTB cases are spontaneous preterm births (sPTBs), an umbrella term for both spontaneous preterm labor (early onset of regular contractions and cervical changes) and preterm premature rupture of the membranes (PPROM, early water breaking). sPTB is difficult to predict, with ongoing studies focused on identifying biological and demographic risk factors as well as potential warning signs during pregnancy. Some studies have suggested that sPTB may be caused by changes in the maternal immune system or in the interplay between the fetal and maternal immune systems.

While early diagnosis and identification of patients at risk for sPTB is an important goal, there are very few therapeutic options available to prevent sPTB. Cervical cerclage, a surgical procedure to close the cervix, has been shown to have some success in preventing sPTB, however, it is an invasive procedure. For pharmacological measures, vaginally-applied progesterone (P4) supplementation has shown some success in preventing PTB in women with short cervixes. In 2011, the United States Food and Drug Administration (FDA) approved injections of hydroxyprogesterone caproate, a synthetic progestin P4, to prevent recurrent sPTB in the USA. However, these treatments have limited success, reducing the risk of PTB by approximately one-third. Accordingly, there remains a need in the art foe new therapies and preventative medicines for PTB.

SUMMARY OF THE INVENTION

Traditional development of novel pharmaceuticals is both expensive and time-consuming. Drug repositioning, or drug "repurposing", is the process of discovering new indications for existing drugs. By searching for new applications of drugs that are already FDA-approved for use in humans, development time and costs can be substantially reduced. Existing drugs have already undergone extensive clinical testing and development and have well-established safety and pharmacokinetic profiles. Some examples of successful repositioning include atomoxetine for attention-deficit hyperactivity disorder (ADHD), sildenafil for erectile dysfunction, and finasteride for hair loss. Safety is an especially important consideration within the context of pregnancies; therefore, by working with existing approved drugs, such as FDA-approved drugs, potential drugs for prevention of sPTB with no known adverse effects to the mother or the fetus could potentially be identified.

With the increasing availability of large public datasets, computational drug repositioning has emerged as a potential approach to identify novel indications for existing drugs. Gene expression microarrays have been used extensively to study genome-wide effects of perturbagens (e.g. drugs) as well as disease states. Differential gene expression profiles can be generated by comparing microarray data from drug-treated samples with those of unperturbed samples. These profiles consist of genes that are up- or down-regulated in cells treated with different compounds relative to those unperturbed. Similarly, disease gene expression signatures can be generated by comparing disease samples with healthy controls. One computational approach utilizes a pattern-matching strategy to find drugs and diseases with opposite differential gene expression profiles—that is, combinations in which genes up- or down-regulated in a disease are down- or up-regulated, respectively, by drug treatment. The hypothesis behind this strategy is that if a disease with a set of gene changes is matched with a drug with the opposite set of gene changes, then that drug could potentially be used therapeutically for the disease.

During pregnancy, the immune system maintains a tolerogenic anti-inflammatory state by proliferating regulatory T-cells until late gestation. At the end of pregnancy, a switch to a pro-inflammatory state promotes labor. To sustain pregnancy, the balance between innate and adaptive immune cells must be maintained, with a premature shift in the balance potentially leading to preterm labor. In a prior study by the inventors of the present disclosure, a cross-study meta-analysis was performed to identify genome-wide differences associated with sPTB, as described in Vora, et al. Meta-Analysis of Maternal and Fetal Transcriptomic Data Elucidates the Role of Adaptive and Innate Immunity in Preterm Birth. *Front Immunol.* 2018;9:993. Pathway analyses of these genes identified enrichment in immune-related pathways, with sPTB associated with the up-regulation of innate immunity and down-regulation of adaptive immunity. In particular, genes that were down-regulated were involved in biological processes including T-cell receptor signaling and transduction, B-cell receptor signaling, leukocyte activation, and lymphocyte activation. Upregulated innate immunity processes included IL-1-signaling and neutrophil degranulation.

With the immune system implicated in sPTB, the inventors of the present disclosure applied a computational drug repositioning approach to drug and disease gene expression profiles to identify potential new treatments for sPTB. FIG. 1 summarizes the general workflow of the repositioning search. Data from the Gene Expression Omnibus (GEO), a public genomics data repository administered by the National Center for Biotechnology Information, contains over 103,000 gene expression studies across 2.6 million microarray samples. Data in GEO was used to first identify a human gene expression profile of sPTB, followed by querying existing drug gene expression profiles (derived from human cell lines) from the Connectivity Map (CMap) and the Library of Integrated Network-Based Cellular Signatures (LINCS) L1000 datasets, resulting in the identification a set of drugs with reversed differential gene expression profiles from that of sPTB. The identified drugs are medications that are all currently used in humans for different indications.

P4, the existing standard for preventing sPTB, is one of the 83 compounds identified in the screen. Of the identified drugs, 81 of these have a higher reversal score than P4. The list was further narrowed down by focusing on those with plausible safety profiles that fall within the pregnancy category A or B designation, yielding a total of 13 potential drugs.

Provided herein are novel therapeutic methods for the prevention of sPTB, by the novel administration of certain known agents to subjects at risk of sPTB, wherein the agents partially reverse gene expression profiles associated with sPTB, creating a therapeutic effect that prevents or treats sPTB. The methods of the invention are described in more detail next.

BRIEF DESCRIPTION OF THE FIGURES

FIG. 3A: Comparisons between pregnancies receiving LPS-100 (n=10), Oil+LPS-100 (n=6), DMSO+LPS-100 (n=7), and saline (n=7) showing a significantly reduced number of viable fetuses at E12.5 in LPS-100 to saline and no significant differences between the LPS-100 group and either of the vehicle groups (Oil+LPS-100 and DMSO+LPS-100). FIG. 3B: The LPS-100 group compared to the P4 positive control group (3×P4+LPS-100) and the lansoprazole treatment group (3×lansoprazole+LPS-100). The P4 positive control group showed some effectiveness, while the lansoprazole treatment was significantly effective in recovering the number of viable fetuses compared with the LPS-100 group.

DETAILED DESCRIPTION OF THE INVENTION

Figure 1:
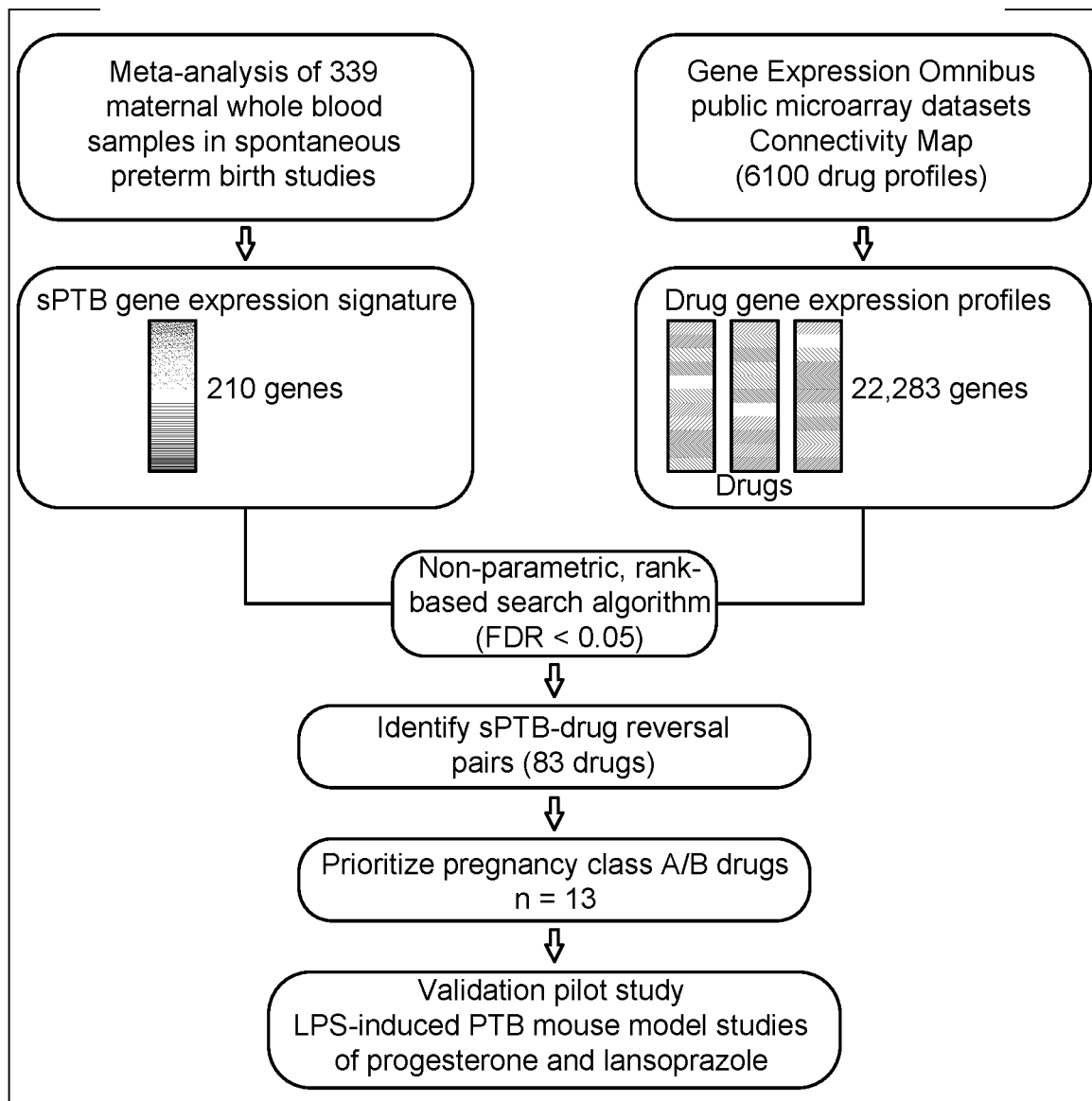
FIG. 1. Depicts the workflow of the drug repositioning search performed herein. The gene expression signature of sPTB was extracted from a meta-analysis of maternal whole blood samples. By comparing the signature with drug gene expression profiles from publicly-available datasets on gene responses to drug exposure, sPTB/drug pairs with reversed gene expressions were identified as therapeutics for PTB FIG. 2. Depicts protein-interaction connectivity of sPTB therapeutic drug hits. The protein interactions of the top ten drug hits identified in the screening method, i.e., those having the highest reversal scores, were analyzed in a drug-protein interaction database, identifying proteins that interact with the identified drugs.

The general method of the invention encompasses a method of treating sPTB in a subject by the novel administration of a therapeutic composition to the subject, wherein the therapeutic composition comprises one or more repurposed drugs having an sPTB gene expression reversal effect. The therapeutic composition is administered in a therapeutically effective amount to a subject at risk of or suffering from sPTB.

As used herein spontaneous preterm birth or sPTB is as known in the art, a condition characterized by delivery at less than thirty seven weeks of pregnancy, as defined by the World Health Organization. As used herein, the "treatment" of sPTB means a treatment that has any beneficial effect in sPTB, including, for example, a treatment that reduces the risk of sPTB, reduces one or more symptoms associated with sPTB, delays delivery by a subject having sPTB symptoms, prevents delivery by a subject having sPTB symptoms, reduces the risk of perinatal mortality, reduces the risk of fetal morbidity or mortality, or otherwise inhibits, ameliorates, or prevents the occurrence of preterm delivery or symptoms associated therewith. Maternal symptoms of sPTB include, preterm labor, preterm spontaneous rupture of membranes, preterm premature rupture of membranes (PPROM), decidual hemorrhage, abruptionuterine overdistention, cervical incompetence, and cervicovaginal infections. Fetal morbidities associated with sPTB include respiratory distress syndrome, neurodevelopmental problems, cerebral palsy, bronchopulmonary dysplasia, seizure disorders, blindness, deafness, and retinopathy of prematurity. In some embodiments, treatment delays delivery, compared to delivery time in untreated mothers undergoing sPTB, which may help the fetus have better post-birth outcomes by allowing developmental advance.

The subject may be any pregnant female animal, including a human or non-human animal species such as a test animal, domestic animal, livestock animal, or veterinary subject, including mice, rats, dogs, cats, cows, horses, and other animals.

In a primary implementation, the treatment is a preventative treatment administered to a subject at risk of sPTB. The treatment may also be an interventional treatment applied to a subject undergoing premature delivery, in order to inhibit delivery, delay delivery, or decrease fetal morbidity or mortality. In one embodiment, the subject at risk of sPTB is a pregnant subject at any stage of pregnancy. In some embodiments, the subject is a pregnant subject at between 8 weeks and 37 weeks, a pregnant subject at between 16 weeks and 37 weeks, a pregnant subject at between 8 weeks and successful delivery, a subject at between 16 weeks and successful delivery, or a subject at any other stage of pregnancy. In another embodiment, the subject is a pre-pregnancy subject, for example, a subject utilizing the sPTB reversing agents of the invention as a pre-pregnancy treatment to reduce the risk of sPTB in a subsequent pregnancy. In one embodiment, the subject is a subject having one or more risk factors of sPTB, including, for example, a subject having prior sPTB history, a subject having a short cervical length, for example, less than 25 mm, a subject having abnormal uterine Doppler flow, Caucasian ethnicity, having a maternal family history of diabetes or preeclampsia, a family history of low birth weight babies, short stature, receipt of hormonal fertility treatment, hypertension, family history of gestational diabetes, and maternal family history of miscarriage, low BMI (for example, a BMI of less than 20). In various embodiments, the subject at risk of sPTB is a subject having any symptoms of premature delivery, including, premature contractions, PPROM, decidual hemorrhage, abruptionuterine overdistention, and other conditions associated with premature delivery.

The treatment encompasses the administration of one or more sPTB-reversing agents. An sPTB-reversing agent is any composition of matter which partially reverses differential gene expression of one or more sPTB genes. An sPTB gene, as used herein, is a gene wherein the expression of the gene is typically altered in subjects having sPTB, for example, being upregulated or downregulated as compared to its expression in pregnant subjects not having sPTB. For example, if a gene's expression is increased in sPTB, the selected sPTB-reversing agent will decrease the expression of the gene, and likewise, if a gene is downregulated in sPTB, the selected sPTB-reversing agent will increase the expression of the sPTB gene. In one embodiment, the sPTB gene is a gene selected from Table 2. With respect to an enumerated sPTB gene, an sPTB-reversing agent is a composition of matter that reverses the sPTB-associated upregulation or downregulation of the gene, for example, partially or wholly reversing the sPTB expression level. In various embodiments, the reversal is at least 10%, at least 20%, at least 30%, at least 40%, at least 50%, at least 60%, at least 70%, at least 80%, at least 90%, or full reversal of the differential expression of the gene observed in sPTB subjects.

In various embodiment, the sPTB-reversing agent is an agent which reverses the expression of multiple sPTB genes comprising an sPTB signature or profile. The sPTB profile comprises a grouping of one or more genes that are upregulated or downregulated in sPTB compared to expression in non-sPTB subjects. In various embodiments, the sPTB signature comprises at least 10, at least 20, at least 30, at least 40, at least 50, at least 60, at least 75, at least 100, at least 125, at least 150, at least 175, or at least 200 sPTB genes, for example, sPTB genes selected from Table 2. In one embodiment, the sPTB signature comprises all or substantially all genes from Table 2.

The sPTB-reversing agent may be any agent having a biological effect encompassing partial offset of an sPTB gene expression profile, meaning any measurable reversal effect for one or more differentially expressed sPTB genes. In various embodiments, the reversal comprises measurable reversal of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, or at least 90% of the genes defining the selected PTB gene expression profile, for example, genes selected from Table 2. in various implementations, the reversal may encompass reversing sPTB-associated differential gene expression of at least five, at least 10, at least 20 at least 50, or at least 100 PTB genes in the selected sPTB gene expression profile, for example an sPTB gene expression profile based on genes in Table 2.

The sPTB-reversing agent will be administered in a therapeutically effective amount. As used herein, a therapeutically effective amount is an amount sufficient to measurably reverse the expression of a selected number or percentage genes in a selected sPTB gene expression profile, for example, at reversing the expression of at least 5, 10, 20, 30, 40, 50, 60, 70, 80, 90, 100, 125, 150, 175, or 200 sPTB genes from the selected signature, for example an sPTB signature comprising at least 25, 50, 75, 100, 125, 150, 175, 200, or all genes of Table 2.

The one or more sPTB-reversing agents may comprise an agent selected from Table 1. The one or more sPTB-reversing agents may be administered in a therapeutic composition. A therapeutic composition is a composition comprising at least one sPTB-reversing agent, and may further comprise any number of additional pharmaceutically acceptable (e.g., biocompatible, safe, and/or well tolerated) constituents, for example, carriers, excipients, fillers, salts, bulking agents, stabilizers, solubilizers, release kinetics modulating compositions, and other compositions suitable for administration of the selected agent.

Any method of administration suitable for the therapeutic composition may be utilized, including by oral, intravenous, subcutaneous, intramuscular, intravaginal (e.g. by cream or suppository), or topical drug delivery routes. Dosages will be selected based on the effective therapeutic range of the selected composition and its toxicity, ADMIT, and other characteristics, as known in the art.

Therapeutic compositions comprising combination products are within the scope of the invention, a combination product being a therapeutic composition comprising two or more sPTB-reversing agents in a single formulation or dosage form, for example, a tablet, capsule, tube, suppository, injection vial, or other dosage form wherein the two or more sPTB-reversing agents are combined. In an alternative implementation, the two or more sPTB-reversing agents are provided together as separate dosage forms, for example, two separate capsules or tablets, for example, packaged in a single packet, box, or other packaging item.

It will be understood that the scope of the invention encompasses sPTB-reversing agents comprising derivatives, analogs, and variants of the sPTB-reversing agents enumerated herein, e.g. any chemical variant of an agent enumerated herein agent which retains substantial level of activity of the parent composition.

TABLE 1 sPTB-reversing agents, cMAP score, and ranking for sPTB gene expression profile reversal.

| Number/rank | name | cmap__score |
|---|---|---|
| 1 | naproxen | −0.4776174 |
| 2 | cefotaxime | −0.4254888 |
| 3 | levopropoxyphene | −0.3999956 |
| 4 | prednisone | −0.3982956 |
| 5 | vorinostat | −0.3968602 |
| 6 | brompheniramine | −0.3881012 |
| 7 | genistein | −0.3841434 |
| 8 | valproic acid | −0.3838569 |
| 9 | cefoperazone | −0.3776029 |
| 10 | alprostadil | −0.3758082 |
| 11 | lansoprazole | −0.3754841 |
| 12 | iopamidol | −0.3737986 |
| 13 | letrozole | −0.3707238 |
| 14 | molindone | −0.364444 |
| 15 | fluticasone | −0.3641804 |
| 16 | estradiol | −0.3641122 |
| 17 | isoxicam | −0.3580252 |
| 18 | thiamphenicol | −0.35371 |
| 19 | guanabenz | −0.3532354 |
| 20 | isometheptene | −0.3524595 |
| 21 | isoniazid | −0.3522468 |
| 22 | sulfadimethoxine | −0.3514506 |
| 23 | ribavirin | −0.3503772 |
| 24 | pioglitazone | −0.3483761 |
| 25 | benzocaine | −0.3426425 |
| 26 | pentoxifylline | −0.3407558 |
| 27 | meclofenamic acid | −0.3390351 |
| 28 | rosiglitazone | −0.3386723 |
| 29 | methotrexate | −0.3378605 |
| 30 | domperidone | −0.3355393 |
| 31 | amitriptyline | −0.3335373 |
| 32 | vinblastine | −0.3309937 |
| 33 | naringenin | −0.3306313 |
| 34 | fulvestrant | −0.3279371 |
| 35 | sodium phenylbutyrate | −0.323206 |
| 36 | haloperidol | −0.3229665 |
| 37 | zalcitabine | −0.3146005 |
| 38 | zuclopenthixol | −0.3145699 |
| 39 | iohexol | −0.3130827 |
| 40 | adenosine phosphate | −0.3109818 |
| 41 | iodixanol | −0.3093972 |
| 42 | viomycin | −0.3082515 |
| 43 | nimodipine | −0.3072987 |
| 44 | ciclosporin | −0.3036273 |

TABLE 1-continued sPTB-reversing agents, cMAP score, and ranking
for sPTB gene expression profile reversal.

| Number/rank | name | cmap_score |
|---|---|---|
| 45 | rifabutin | −0.3023398 |
| 46 | podophyllotoxin | −0.301874 |
| 47 | ceforanide | −0.300357 |
| 48 | sirolimus | −0.3001623 |
| 49 | ajmaline | −0.2991141 |
| 50 | diloxanide | −0.2978555 |
| 51 | chlortalidone | −0.2975129 |
| 52 | trimethobenzamide | −0.2973518 |
| 53 | timolol | −0.2961973 |
| 54 | tenoxicam | −0.295402 |
| 55 | ketotifen | −0.2953538 |
| 56 | geldanamycin | −0.2933835 |
| 57 | dantrolene | −0.2900623 |
| 58 | dapsone | −0.2874828 |
| 59 | streptozocin | −0.2860236 |
| 60 | raloxifene | −0.2852901 |
| 61 | ambroxol | −0.2839382 |
| 62 | benzathine benzylpenicillin | −0.283031 |
| 63 | finasteride | −0.2753629 |
| 64 | trifluoperazine | −0.2744129 |
| 65 | vanoxerine | −0.2720786 |
| 66 | thiamazole | −0.2718269 |
| 67 | homosalate | −0.26783 |
| 68 | levomepromazine | −0.2675083 |
| 69 | co-dergocrine mesilate | −0.2675047 |
| 70 | oxyphenbutazone | −0.2674383 |
| 71 | promazine | −0.2673037 |
| 72 | metformin | −0.266853 |
| 73 | carisoprodol | −0.2665583 |
| 74 | niclosamide | −0.2658271 |
| 75 | methoxamine | −0.2651377 |
| 76 | folic acid | −0.2641576 |
| 77 | clotrimazole | −0.2637673 |
| 78 | tocainide | −0.2630803 |
| 79 | cefotiam | −0.2607573 |
| 80 | maprotiline | −0.258529 |
| 81 | resveratrol | −0.257993 |
| 82 | progesterone | −0.2560183 |
| 83 | nadolol | −0.2545566 |

Specific Implementations of the Invention. In a primary implementation, the scope of the invention encompasses a therapeutic composition for use in a method of treating sPTB, comprising one or more agents that partially reverse the gene expression profile associated with sPTB. In a related embodiment, the scope of the invention encompasses a method of treating sPTB in a subject in need of treatment therefor by the administration to the subject of a therapeutic composition comprising a therapeutically effective amount of one or more agents that partially reverse the gene expression profile associated with sPTB. In another aspect, the scope of the invention encompasses a method of making a medicament for use in the treatment of sPTB comprising the use of one or more agents that partially reverse the gene expression profile associated with sPTB. In various embodiments, the one or more agents that partially reverse the gene expression profile associated with sPTB is selected from Table 2. In various embodiments, the treatment is a preventative treatment that reduces the risk of sPTB or ameliorates the severity of one or more sPTB symptoms. In various embodiments, the subject is a subject that is pregnant, for example, a subject having one or more risk factors or symptoms of sPTB. In various embodiments, the treatment is interventional, administered to a subject undergoing or having a symptom of premature delivery.

The scope of the invention encompasses a therapeutic composition for use in a method of treating sPTB, comprising one or more agents that partially reverse the gene expression profile associated with sPTB selected from the group consisting of: naproxen, cefotaxime, levopropoxyphene, prednisone, vorinostat, brompheniramine, genistein, valproic acid, cefoperazone, alprostadil, lansoprazole, iopamidol, letrozole, molindone, fluticasone, estradiol, isoxicam, thiamphenicol, guanabenz, isometheptene, isoniazid, sulfadimethoxine, ribavirin, pioglitazone, benzocaine, pentoxifylline, meclofenamic acid, rosiglitazone, methotrexate, domperidone, amitriptyline, vinblastine, naringenin, fulvestrant, sodium phenylbutyrate, haloperidol, zalcitabine, zuclopenthixol, iohexol, adenosine phosphate, iodixanol, viomycin, nimodipine, ciclosporin, rifabutin, podophyllotoxin, ceforanide, sirolimus, ajmaline, diloxanide, chlortalidone, trimethobenzamide, timolol, tenoxicam, ketotifen, geldanamycin, dantrolene, dapsone, streptozocin, raloxifene, ambroxol, benzathine benzylpenicillin, finasteride, trifluoperazine, vanoxerine, thiamazole, homosalate, levomepromazine, co-dergocrine mesilate, oxyphenbutazone, promazine, carisoprodol, niclosamide, methoxamine, tocainide, cefotiam, maprotiline, resveratrol, progesterone, and nadolol. In one embodiment, the agent is lansoprazole. In one embodiment, the agent is cefotaxime. In one embodiment, the agent is rifabutin. In one embodiment, the agent is chlortalidone. In one embodiment, the agent is benzathine benzylpenicillin. In one embodiment, the agent is maprotiline. In one embodiment, the agent is naproxen.

In other embodiments, the agent that partially reverses the gene expression profile associated with sPTB is metformin, folic acid, or clotrimazole.

In related implementations, the scope of the invention encompasses a method of treating sPTB in a subject in need of treatment therefor by the administration to the subject of a therapeutic composition comprising a therapeutically effective amount one or more agents selected from the group consisting of: naproxen, cefotaxime, levopropoxyphene, prednisone, vorinostat, brompheniramine, genistein, valproic acid, cefoperazone, alprostadil, lansoprazole, iopamidol, letrozole, molindone, fluticasone, estradiol, isoxicam, thiamphenicol, guanabenz, isometheptene, isoniazid, sulfadimethoxine, ribavirin, pioglitazone, benzocaine, pentoxifylline, meclofenamic acid, rosiglitazone, methotrexate, domperidone, amitriptyline, vinblastine, naringenin, fulvestrant, sodium phenylbutyrate, haloperidol, zalcitabine, zuclopenthixol, iohexol, adenosine phosphate, iodixanol, viomycin, nimodipine, ciclosporin, rifabutin, podophyllotoxin, ceforanide, sirolimus, ajmaline, diloxanide, chlortalidone, trimethobenzamide, timolol, tenoxicam, ketotifen, geldanamycin, dantrolene, dapsone, streptozocin, raloxifene, ambroxol, benzathine benzylpenicillin, finasteride, trifluoperazine, vanoxerine, thiamazole, homosalate, levomepromazine, co-dergocrine mesilate, oxyphenbutazone, promazine, metformin, carisoprodol, niclosamide, methoxamine, folic acid, clotrimazole, tocainide, cefotiam, maprotiline, resveratrol, progesterone, and nadolol. In one embodiment, the agent is lansoprazole. In one embodiment, the agent is cefotaxime. In one embodiment, the agent is rifabutin. In one embodiment, the agent is chlortalidone. In one embodiment, the agent is benzathine benzylpenicillin. In one embodiment, the agent is maprotiline. In one embodiment, the agent is naproxen.

In one embodiment, the scope of the invention encompasses a therapeutic composition for use in a method of treating sPTB, the therapeutic comprising lansoprazole. In a related embodiment, the scope of the invention encompasses a method of treating sPTB in a subject in need of treatment therefor by the administration to the subject of a therapeutic composition comprising a therapeutically effective amount of lansoprazole, for example lansoprazole administered at a dosage of 0.1-5 mg/kg/day, for example, 0.5 to 1.5 mg/kg/day, for example, formulated for oral delivery and administered orally.

In one embodiment, the scope of the invention encompasses a therapeutic composition for use in a method of treating sPTB, the therapeutic comprising cefotaxime. In a related embodiment, the scope of the invention encompasses a method of treating sPTB in a subject in need of treatment therefor by the administration to the subject of a therapeutic composition comprising a therapeutically effective amount of cefotaxime, for example cefotaxime administered at a dosage of 20-200 mg/kg/day, for example, 50-180 mg/kg/day, for example, formulated for intravenous or intramuscular injection delivery and administered by intravenous or intramuscular injection.

In one embodiment, the scope of the invention encompasses a therapeutic composition for use in a method of treating sPTB, the therapeutic comprising rifabutin. In a related embodiment, the scope of the invention encompasses a method of treating sPTB in a subject in need of treatment therefor by the administration to the subject of a therapeutic composition comprising a therapeutically effective amount of rifabutin, for example rifabutin administered at a dosage of 5-50 mg/kg/day, for example, formulated. for oral delivery and administered orally.

In one embodiment, the scope of the invention encompasses a therapeutic composition for use in a method of treating sPTB, the therapeutic comprising chlortalidone, also known as chlorthalidone. in a related embodiment, the scope of the invention encompasses a method of treating sPTB in a subject in need of treatment therefor by the administration to the subject of a therapeutic composition comprising a therapeutically effective amount of chlortalidone, for example chlortalidone administered at a dosage of 25-100 mg/kg/day, for example, formulated for oral delivery and administered orally.

In one embodiment, the scope of the invention encompasses a therapeutic composition for use in a method of treating sPTB, the therapeutic comprising benzathine benzylpenicillin. In a related embodiment, the scope of the invention encompasses a method of treating sPTB in a subject in need of treatment therefor by the administration to the subject of a therapeutic composition comprising a therapeutically effective amount of benzathine benzylpenicillin, for example chlortalidone administered at a dosage of 25-100 mg/kg/day, for example, 1-3 million International Units, for example, formulated for oral delivery and administered orally.

In one embodiment, the scope of the invention encompasses a therapeutic composition for use in a method of treating sPTB, the therapeutic comprising metformin. In a related embodiment, the scope of the invention encompasses a method of treating sPTB in a subject in need of treatment therefor by the administration to the subject of a therapeutic composition comprising a therapeutically effective amount of metformin, for example metformin administered at a dosage of 10-100 mg/kg/day, for example, 2050 mg/kg/day, for example, formulated for oral delivery and administered orally In one embodiment, the scope of the invention encompasses a therapeutic composition for use in a method of treating sPTB, the therapeutic comprising folic acid or folate. In a related embodiment, the scope of the invention encompasses a method of treating sPTB in a subject in need of treatment therefor by the administration to the subject of a therapeutic composition comprising a therapeutically effective amount of folic acid, for example folic acid administered at a dosage of 1-5 mg/kg/day, for example, formulated for oral delivery and administered orally.

In one embodiment, the scope of the invention encompasses a therapeutic composition for use in a method of treating sPTB, the therapeutic comprising clotrimazole. In a related embodiment, the scope of the invention encompasses a method of treating sPTB in a subject in need of treatment therefor by the administration to the subject of a therapeutic composition comprising a therapeutically effective amount of clotrimazole, for example clotrimazole administered at a dosage of 1-50 mg/kg/day, for example, 5-10 mg/kg/day, for example, formulated for oral delivery and administered orally or formulated for topical delivery, for example, as a vaginal cream or vaginal suppository.

In one embodiment, the scope of the invention encompasses a therapeutic composition for use in a method of treating sPTB, the therapeutic comprising maprotiline. In a related embodiment, the scope of the invention encompasses a method of treating sPTB in a subject in need of treatment therefor by the administration to the subject of a therapeutic composition comprising a therapeutically effective amount of maprotiline, for example maprotiline administered at a dosage of 1-50 mg/kg/day, for example 10-25 mg/kg/day, for example, formulated for oral delivery and administered orally.

In one embodiment, the scope of the invention encompasses a therapeutic composition for use in a method of treating sPTB, the therapeutic comprising naproxen. In a related embodiment, the scope of the invention encompasses a method of treating sPTB in a subject in need of treatment therefor by the administration to the subject of a therapeutic composition comprising a therapeutically effective amount of naproxen, for example maprotiline administered at a dosage of 1-10 mg/kg/day, for example 2-5 mg/kg/day, for example, formulated for oral delivery and administered orally. Additional sPTB-reversing agents include: antihistamines antipsychotics, antidiabetics, adrenergic agonists, nonsteroidal anti-inflammatory compositions, antibiotics, antifungals, proton-pump inhibitors, calcium channel blockers, modulators, including inhibitors, of CYP1A2, modulators, including inhibitors, of CYP3A4, modulators, including inhibitors, of CYP2C9, modulators, including inhibitors, of CYP2D6, modulators, including inhibitors, of multidrug resistance protein 1 (MDR1), modulators, including inhibitors, of dopamine receptor $D_2$ (D2R), modulators, including inhibitors, of histamine receptor $H_1$ (HRH1), and modulators, including inhibitors, of prostaglandin G/H synthase 1 (PTGS1).

EXAMPLES

Example 1 Computational Discovery of Therapeutic Candidates for Preventing Preterm Birth A bioinformatics approach was applied leveraging publicly-available transcriptomic data to identify potential new treatments for sPTB. This computational pipeline scored the reversal between two lists of differentially expressed genes, with the hypothesis that an sPTB-drug pair with a negative reversal score indicated the drug could be therapeutic for sPTB. The gene expression signature of sPTB was scored with each drug in CMap, resulting in a list of 83 sPTB-drug pairs with a significant reversal score. The list was narrowed down by focusing on 6 drugs belonging to pregnancy category B.

Gene expression signature of sPTB. As described in Vora et al., a cross-study meta-analysis identifying genome-wide differential gene expression signals in sPTB is known. Three studies (GSE46510, GSE59491, and GSE73685) relating to sPTB were identified in GEO. These studies analyzed a total of 339 whole blood samples from women delivering prematurely (n=134) or at term (n=205). The three studies were aggregated together and then corrected for batch effects, resulting in a normalized dataset of 4,648 genes after applying a false discovery rate (FDR) of 0.1. After applying a threshold of a 1.3-fold increase or decrease in differential gene expression, the gene list was further reduced to a final set containing 210 genes (65 up- and 145 down-regulated, Table 2).

Gene expression profiles of drugs. Differential gene expression profiles for drugs were collected from two complementary sources: CMap (GSE70138), as described in Lamb J, et al. The Connectivity Map: using gene-expression signatures to connect small molecules, genes, and disease. *Science*. 2006;313(5795):1929-1935 and the LINCS L1000 dataset, as described in Subramanian et al. A Next Generation Connectivity Map: L1000 platform and the first 1,000, 000 profiles. *Cell*. 2017;171(6):1437-1452.e17. Both are collections of differential gene expression profiles of cultured human cells treated with a variety of small molecule perturbagens. Using DNA microarrays to assay mRNA expression, the creators of CMap generated a broad database cataloging the effects of drugs on genes. CMap is a deep, genome-wide profiling of the effects of approximately 1,300 drugs on a variety of cell lines. The LINCS L1000 dataset can be characterized as a shallow profiling (978 genes) of over 10,000 drugs. While the depth of the CMap dataset and the breadth of the LINCS L1000 dataset provide two complementary views into the effects of drugs on gene expression, the genome-wide aspect of the CMap was utilized in the present disclosure. Of the 210 differentially-expressed genes identified by the sPTB meta-analysis study, 159 were also profiled in CMap, while only 16 were profiled in LINCS. As a result, the present disclosure combined the sPTB gene expression signature with the drug gene expression profiles from CMap.

Computational gene expression pattern matching. To identify potential therapeutic drugs, a non-parametric rank-based method was used to identify candidates based on differential gene expression profiles as described in Sirota M, et al. Discovery and Preclinical Validation of Drug Indications Using Compendia of Public Gene Expression Data. *Science Translational Medicine*. 2011;3(96):96ra77; Dudley JT, et al. Computational Repositioning of the Anticonvulsant Topiramate for Inflammatory Bowel Disease. *Science Translational Medicine*. 2011;3(96):96ra76; Chen B, et al. Computational Discovery of Niclosamide Ethanolamine, a Repurposed Drug Candidate That Reduces Growth of Hepatocellular Carcinoma Cells In Vitro and in Mice by Inhibiting Cell Division Cycle 37 Signaling. *Gastroenterology*. 2017;152(8):2022-2036; and Chen B, et al. Reversal of cancer gene expression correlates with drug efficacy and reveals therapeutic targets. *Nature Communications*. 2017;8:16022. The goal was to identify drugs with gene changes that are the reverse of those observed in sPTB. Based on the Kolmogorov-Smirnov statistic, this type of analysis was originally suggested by Lamb et al. in their original publication of the CMap database. This was extended and applied in the present study to specifically identify new uses for existing drugs. Build 02 version of CMap was used to obtain genome-wide gene expression profiles (relative to controls) from a variety of cell lines treated with small-molecule perturbagens. This database provided differential gene expression profiles (~22,000 genes) for 1,309 drugs/compounds cultured in up to 5 different cell lines. A total of 6,100 drugs were tested with variations in both concentrations and durations of treatment. A pre-filtering step was applied for the profiles similar to a previous computational drug repurposing pipeline. Of the 210 differentially-expressed genes identified by the cross-study meta-analysis, 159 (44 up- and 115 down-regulated, Table 2) were present in the drug gene expression profiles in CMap. Drugs were given scores based on the relationship between their differential gene expression profiles relative to the sPTB gene expression profile. A negative score indicated a reverse profile between the drug and sPTB, where the up-regulated genes in sPTB were lower ranked (more down-regulated) and the down-regulated genes in sPTB were higher ranked (more up-regulated) in the drug profiles. Conversely, a positive score indicated a similar profile between the drug and sPTB. Significances of scores were obtained by a comparison to a distribution of scores generated from random permutations and then adjusted for multiple comparisons; only scores with FDR<0.05 were kept. For drugs with multiple gene expression profiles (from testing on different cell lines and dosages), the profile with the lowest negative (most reversed) score was used.

Statistical Analysis. Reversal scores were generated for sPTB-drug pairs using a non-parametric, rank-based method based on the Kolgomorov-Smirnov test. Reversal score p-values were obtained by comparing to a distribution of 100,000 random scores and then adjusted via FDR for multiple comparisons. An individual random score was generated by selecting a random subset of genes matching the disease signature (44 ranked up-regulated genes, 115 ranked down-regulated genes) from the entire CMap gene list to act as a proxy signature and then compared to a random CMap drug for score calculation. To ensure that the significance of the score is specific to the drug in question, for one candidate drug, lansoprazole, we also compared 1,000 random input signatures to the lansoprazole profile. The PTB reversal score for lansoprazole was more extreme than each of the 1,000 generated random scores for lansoprazole, highlighting the significance of the findings. For testing the distributions in the mouse model studies, comparisons were made using the 2-tailed Student's t-test and adjusted via FDR for multiple comparisons. A P value less than 0.05 was considered significant.

Results. Computational identification of drug repositioning candidates. By comparing the drug signatures from CMap with the differential gene expression for sPTB, 83 sPTB-reversing drugs were identified, including P4, which significantly reversed the disease gene expression signature. This list can be narrowed down by safety profiles during pregnancy. In the past, the FDA applied broad labels known as pregnancy categories to drugs based on results from both human and animal studies. Letter grades of categories were broadly based upon risk to the pregnant mother and her fetus. Pregnancy category B corresponds to drugs that have failed to demonstrate risk in animal studies with no adequate studies in pregnant women, while pregnancy category A is reserved for drugs for which human studies have failed to demonstrate a risk. By ruling out drugs with no known pregnancy category and drugs with pregnancy categories with positive evidence of risk, a subset of thirteen category A or category B compounds was identified, including cefotaxime, lansoprazole, iopamidol, iohexol, iodixanol, rifabutin, chlorotalidone, benzathine benzylpenicillin, metformin, folic acid, chotrimazole, maprotiline, and progesterone.

Notably, P4 is one of the thirteen drug hits identified. Only one pregnancy category A drug was identified: folic acid. Belonging to pregnancy category B are P4 and 11 of the other drugs: three antibiotics (benzathine benzylpenicillin and cefotaxime, and rifabutin), an antifungal (clotrimazole), a PPI (lansoprazole), an antidepressant (maprotiline), an anti-diabetic (metformin), an antihypertensive (chlortalidone), and three contrast agents (iopamidol, iohexol, and iodixanol). Each of the compounds exhibited a clear reversal of the sPTB gene expression signature.

Figure 2:
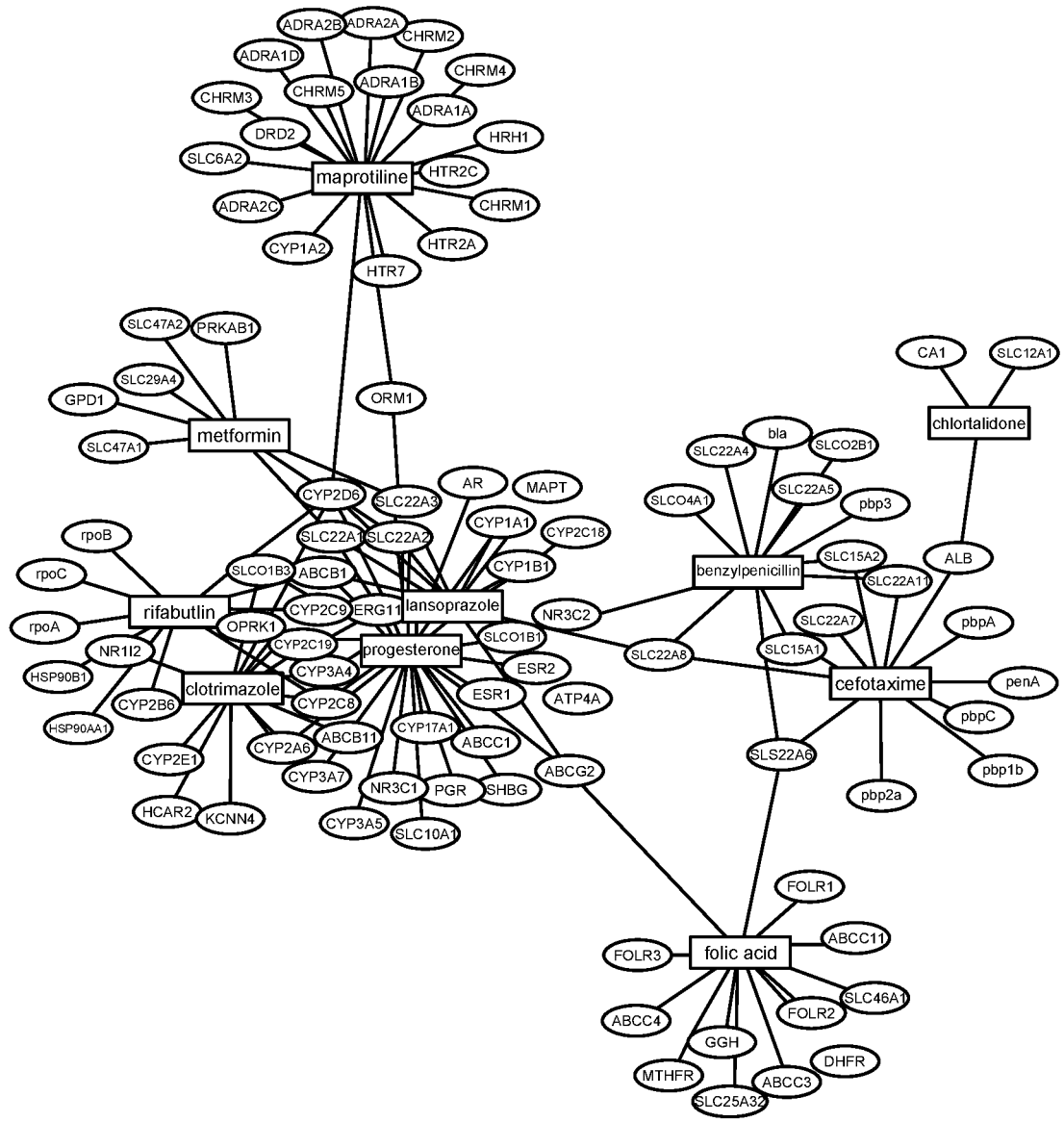

Common protein interactions among 13 pregnancy category A/B drug hits. Using DrugBank as a reference, 27 proteins that interact with at least 2 of the drug hits were identified. By using these interactions to construct a network (FIG. 2), shared interactions between the drug hits can be visualized (with no interactions recorded for the three contrast agents). Common proteins include members of the cytochrome P450 family (most commonly CYP2D6), members of solute carrier family 22, and multidrug resistance protein 1 (ABCB1). Cytochrome P450 1B1 (CYP1B1) is the only common protein that is also shared by the PTB signature.

Figure 3B:
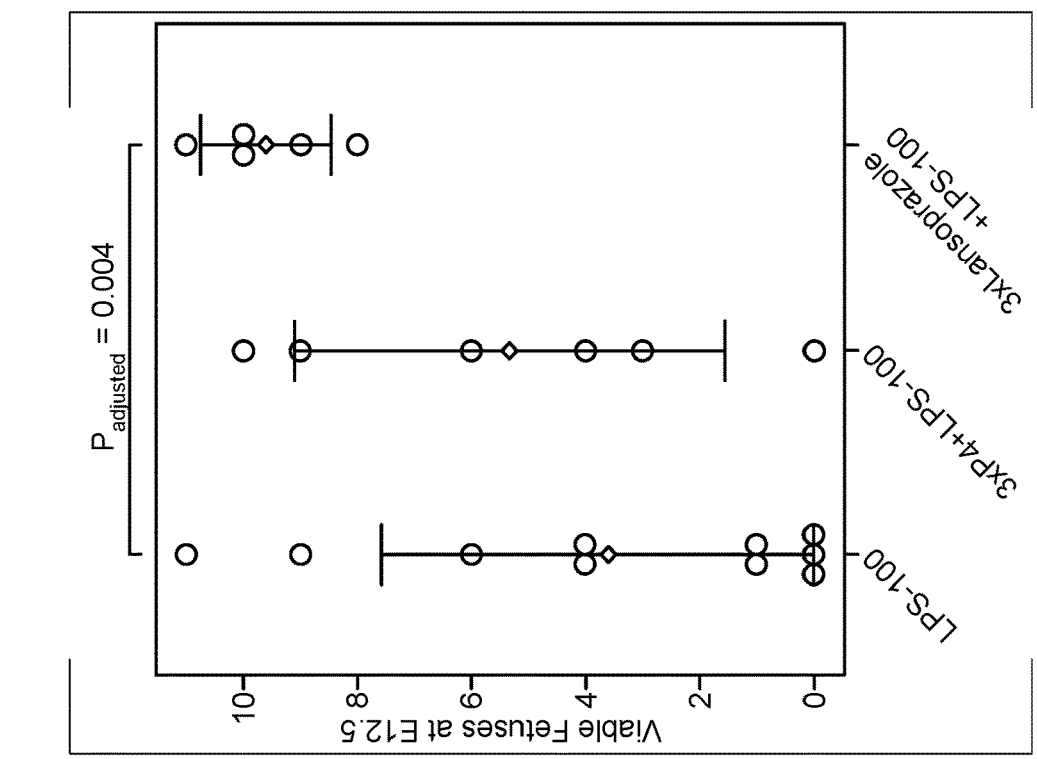
FIG. 3A and FIG. 3B depict results from LPS-induced inflammation mouse model of fetal wastage. Circles represent results from independent mouse pregnancies. Error bars represent mean ±SD. Comparisons were made using the Student's two-sided t-test.
Figure 3A:
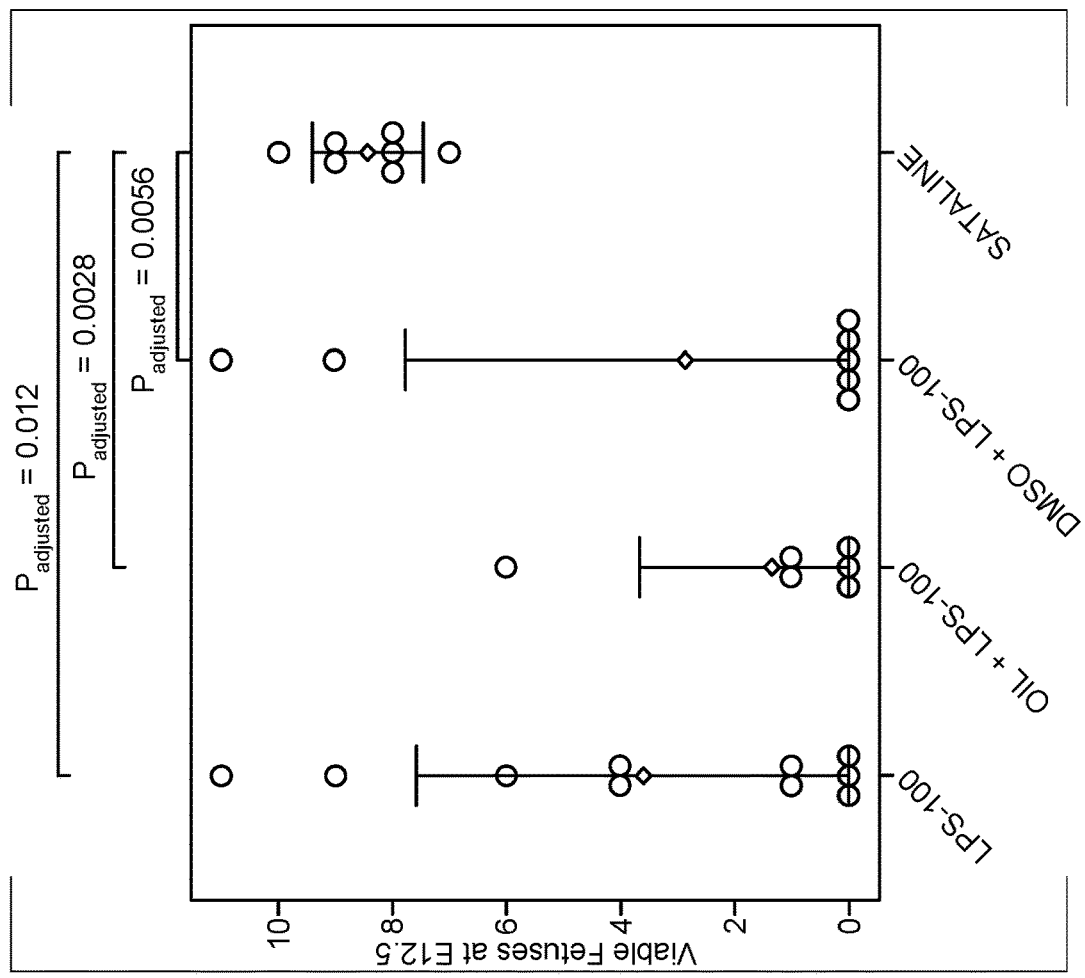

Inflammation-induced mouse model validation of lansoprazole. Despite having the highest reversal score, cefotaxime shares few protein interactions. Lansoprazole has the next highest reversal score. Moreover, lansoprazole is available over-the-counter, whereas cefotaxime requires a prescription. Lansoprazole has also been connected to the stress-response protein heme oxygenase-1 (HO-1), and deficiencies in HO-1 have been linked with pregnancy disorders. Thus, a validation study of lansoprazole was conducted. A mouse model of inflammation using LPS to induce fetal wastage in pregnant mice was employed. In addition to lansoprazole, P4 was tested as a positive control since it is currently indicated for the prevention of sPTB. The counts of viable mouse fetuses at E12.5 for each treatment group are summarized in FIG. 3A and 3B. The LPS-100 group had significantly ($p<0.05$) fewer viable fetuses compared to the saline group, demonstrating the effectiveness of the LPS-induced model. Treatment with oil (oil+LPS-100) alone (P4 vehicle) had no effect on fetal viability. The positive control group (3×P4+LPS-100) showed some effectiveness at recovering the number of viable fetuses at E12.5. Lastly, LPS-100 alone was compared to the lansoprazole group (3×lansoprazole+LPS-100). The lansoprazole group was able to significantly ($P<0.05$) increase the number of viable fetuses compared with LPS-100 alone. Treatment with 5% DMSO (DMSO+LPS-100) alone (lansoprazole vehicle) had no effect on fetal viability.

The experiments disclosed herein identified existing drugs for repositioning by applying a computational approach to transcriptomics. By comparing the differential gene expression signature for sPTB (derived from maternal blood samples) with the differential gene expression profiles of drug experiments (derived from human cell lines), 83 drugs were found whose profiles were significantly reversed compared to sPTB. As the data were derived from human gene expression, the physiology of sPTB should be especially represented in the drug predictions. Thirteen of these drugs—benzathine benzylpenicillin, cefotaxime, chlortalidone, clotrimazole, folic acid, iodixanol, iohexol, iopamidol, lansoprazole, maprotiline, metformin, P4, and rifabutin—belong to pregnancy category A or B, indicating no known risk in pregnant women.

P4, clotrimazole, metformin, and folic acid have shown some efficacy against PTB in past studies. P4 treatment has been shown to be effective in reducing the rate of sPTB in cases where pregnant women have short cervixes, as described in Fonseca et al., Fetal Medicine Foundation Second Trimester Screening Group. Progesterone and the risk of preterm birth among women with a short cervix. *N Engl J Med.* 2007;357(5):462-469. Clotrimazole, an antifungal with no teratogenic effects, is used to treat yeast and fungal infections. An analysis of 17 years of Hungarian births found that mothers receiving clotrimazole treatment during pregnancy tended to have longer pregnancies, with a significant reduction in the rate of PTB, suggesting a protective effect that could not be explained by other factors, as described in Czeizel et al., Preterm birth reduction after clotrimazole treatment during pregnancy. *Eur J Obstet Gynecol Reprod Biol.* 2004;116(2):157-163. Metformin, an anti-diabetic, has been found to reduce the rate of PTB compared with placebo in women with polycystic ovary syndrome, as described in Vanky et al., On the potential of metformin to prevent preterm delivery in women with polycystic ovary syndrome—an epi-analysis. *Acta Obstetricia et Gynecologica Scandinavica.* 2012;91(12):1460-1464. Folic acid, commonly taken during early pregnancy, was observed to have a possible reduction of preterm birth in another Hungarian population study, Czeizel et al., Possible association of folic acid supplementation during pregnancy with reduction of preterm birth: a population-based study. *Eur J Obstet Gynecol Reprod Biol.* 2010; 148(2):135-140.

In summary, a computational drug repurposing analysis was applied to identify potential novel therapeutics for the prevention of PTB. In addition to P4, the only drug currently used to prevent recurrent sPTB, twelve other plausible candidates were identified with no known safety risk in pregnancy. Lansoprazole was validated in pilot studies on an LPS-induced inflammation mouse model. These results demonstrate the novel therapeutic application of lansoprazole the other drug hits identified by the analysis in preventing sPTB.

TABLE 2

Differentially Expressed Genes in sPTB.

| Gene | Directionality |
| --- | --- |
| LRRN3 | Downregulated |
| FCER1A | Downregulated |
| TRAT1 | Downregulated |
| LDHB | Downregulated |
| CLC | Downregulated |
| ZNF83 | Downregulated |
| STAP1 | Downregulated |
| CLEC12A | Downregulated |
| GBP3 | Downregulated |
| BLNK | Downregulated |
| RWDD3 | Downregulated |
| ACADM | Downregulated |
| ABCE1 | Downregulated |
| CCDC91 | Downregulated |
| NELL2 | Downregulated |
| MS4A1 | Downregulated |
| SSB | Downregulated |
| CASP8AP2 | Downregulated |
| EBAG9 | Downregulated |
| TSPAN13 | Downregulated |
| METTL18 | Downregulated |
| PMAIP1 | Downregulated |
| C9orf78 | Downregulated |
| ANKRD46 | Downregulated |
| ZBTB41 | Downregulated |
| TRMT61B | Downregulated |
| EIF3E | Downregulated |
| ZNF664 | Downregulated |
| C8orf59 | Downregulated |
| DBF4 | Downregulated |

TABLE 2-continued

Differentially Expressed Genes in sPTB.

| Gene | Directionality |
|---|---|
| RANBP6 | Downregulated |
| DCK | Downregulated |
| ABCB10 | Downregulated |
| SUCLA2 | Downregulated |
| INPP4B | Downregulated |
| RASGRP1 | Downregulated |
| EIF2A | Downregulated |
| LRRC40 | Downregulated |
| ASF1A | Downregulated |
| ZFAND1 | Downregulated |
| ISCA1 | Downregulated |
| HMGN3 | Downregulated |
| GOLGA8A | Downregulated |
| THEMIS | Downregulated |
| IER3IP1 | Downregulated |
| ISOC1 | Downregulated |
| NUCB2 | Downregulated |
| TRAJ41 | Downregulated |
| SLC18B1 | Downregulated |
| RPIA | Downregulated |
| HEBP1 | Downregulated |
| UBE2Q2 | Downregulated |
| CD3D | Downregulated |
| CCNC | Downregulated |
| NDUFA5 | Downregulated |
| CMAS | Downregulated |
| CAMK4 | Downregulated |
| RWDD1 | Downregulated |
| TCEAL8 | Downregulated |
| ITK | Downregulated |
| RAN | Downregulated |
| SLFN5 | Downregulated |
| CD8B | Downregulated |
| TXK | Downregulated |
| TRABD2A | Downregulated |
| TMEM14C | Downregulated |
| TRAC | Downregulated |
| CD3G | Downregulated |
| MTERF3 | Downregulated |
| PLEKHA1 | Downregulated |
| ADRB2 | Downregulated |
| TCF7 | Downregulated |
| FAM210B | Downregulated |
| OXNAD1 | Downregulated |
| GCLC | Downregulated |
| CPOX | Downregulated |
| CD96 | Downregulated |
| PRDX2 | Downregulated |
| CDR2 | Downregulated |
| FAM102A | Downregulated |
| SERPINI1 | Downregulated |
| PITHD1 | Downregulated |
| SCML1 | Downregulated |
| RALGAPA1 | Downregulated |
| ITGA6 | Downregulated |
| LCK | Downregulated |
| ANP32B | Downregulated |
| DNAJA4 | Downregulated |
| PCMTD2 | Downregulated |
| ANKH | Downregulated |
| ODC1 | Downregulated |
| RGCC | Downregulated |
| ITGA4 | Downregulated |
| LEF1 | Downregulated |
| GCSAM | Downregulated |
| LSM5 | Downregulated |
| SELENBP1 | Downregulated |
| SSBP3 | Downregulated |
| MBNL3 | Downregulated |
| GSDMB | Downregulated |
| DYNC1I2 | Downregulated |
| AK5 | Downregulated |
| DPP4 | Downregulated |
| ESYT1 | Downregulated |
| ACP1 | Downregulated |
| CD28 | Downregulated |
| FUCA1 | Downregulated |
| TESPA1 | Downregulated |
| C11orf1 | Downregulated |
| RPS27A | Downregulated |
| TBCEL | Downregulated |
| CCR7 | Downregulated |
| SESN3 | Downregulated |
| NPAT | Downregulated |
| ZMAT2 | Downregulated |
| TRAV5 | Downregulated |
| TMEM245 | Downregulated |
| CETN2 | Downregulated |
| VTI1B | Downregulated |
| TFDP2 | Downregulated |
| PDE4DIP | Downregulated |
| VSIG1 | Downregulated |
| EPB41 | Downregulated |
| MKRN1 | Downregulated |
| RNF144A | Downregulated |
| SATB1 | Downregulated |
| ZNF792 | Downregulated |
| LDLRAP1 | Downregulated |
| PHLPP2 | Downregulated |
| CCND2 | Downregulated |
| GRAP | Downregulated |
| ATF7IP2 | Downregulated |
| UBE3D | Downregulated |
| N6AMT1 | Downregulated |
| DCTN5 | Downregulated |
| TNIK | Downregulated |
| ZKSCAN8 | Downregulated |
| ZNF77 | Downregulated |
| CAMKMT | Downregulated |
| MYH11 | Upregulated |
| BAIAP2L1 | Upregulated |
| TXLNGY | Upregulated |
| LAMB2 | Upregulated |
| KCNMA1 | Upregulated |
| STS | Upregulated |
| LHX4 | Upregulated |
| TFPI | Upregulated |
| GABRR2 | Upregulated |
| SSH1 | Upregulated |
| GPER1 | Upregulated |
| LSMEM1 | Upregulated |
| NFKBIA | Upregulated |
| RAB3D | Upregulated |
| OFCC1 | Upregulated |
| SIGLEC9 | Upregulated |
| HPSE | Upregulated |
| LOC728175 | Upregulated |
| MGAM2 | Upregulated |
| SLC8A1 | Upregulated |
| HOXA-AS2 | Upregulated |
| ZNF438 | Upregulated |
| IL1RAP | Upregulated |
| TMEM88 | Upregulated |
| MKNK1 | Upregulated |
| HRH2 | Upregulated |
| ETS2 | Upregulated |
| IL1R1 | Upregulated |
| NLRP3 | Upregulated |
| ATP13A3 | Upregulated |
| EXT1 | Upregulated |
| SPI1 | Upregulated |
| SLC1A3 | Upregulated |
| SLC51A | Upregulated |
| IRAK3 | Upregulated |
| HK3 | Upregulated |
| CYP1B1 | Upregulated |
| TLR5 | Upregulated |
| GYG1 | Upregulated |
| GAS7 | Upregulated |
| LRG1 | Upregulated |
| NECAB1 | Upregulated |
| PFKFB2 | Upregulated |

TABLE 2-continued

Differentially Expressed Genes in sPTB.

| Gene | Directionality |
|---|---|
| CLEC4D | Upregulated |
| ALPL | Upregulated |
| SOCS3 | Upregulated |
| GPR84 | Upregulated |
| NLRC4 | Upregulated |
| LINC00189 | Upregulated |
| CASP5 | Upregulated |
| IL1R2 | Upregulated |
| FKBP5 | Upregulated |
| OPLAH | Upregulated |
| SLC26A8 | Upregulated |
| NSUN7 | Upregulated |
| GRB10 | Upregulated |
| GALNT14 | Upregulated |
| TDRD9 | Upregulated |
| TMTC1 | Upregulated |
| ZDHHC19 | Upregulated |
| RPH3A | Upregulated |
| CD177 | Upregulated |

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

The invention claimed is:

1. A method of treating spontaneous preterm birth in a subject in need of treatment therefor by the administration to the subject of a therapeutic composition comprising a therapeutically effective amount of one or more agents that partially reverse the gene expression profile associated with spontaneous preterm birth.

2. The method of claim 1, wherein the subject is a subject at any stage of pregnancy.

3. The method of claim 1, wherein the subject is a subject having one or more risk factors or symptoms of spontaneous preterm birth.

4. The method of claim 1, wherein the treatment is a preventative treatment.

5. The method of claim 1, wherein the therapeutic composition comprises an agent that partially reverses the gene expression profile associated with spontaneous preterm birth selected from the group consisting of: naproxen, cefotaxime, levopropoxyphene, prednisone, vorinostat, brompheniramine, genistein, valproic acid, cefoperazone, alprostadil, lansoprazole, iopamidol, letrozole, molindone, fluticasone, estradiol, isoxicam, thiamphenicol, guanabenz, isomethepteue, isoniazid, sulfadimethoxine, ribavirin, pioglitazone, benzocaine, pentoxifylline, meclofenamic acid, rosiglitazone, methotrexate, domperidone, amitriptyline, vinblastine, naringenin, fulvestrant, sodium phenylbutyrate, haloperidol, zalcitabine, zuclopenthixol, iohexol, adenosine phosphate, iodixanol, viomycin, nimodipine, ciclosporin, rifabutin, podophyllotoxin, ceforanide, sirolimus, ajmaline, diloxanide, chlortalidone, trimethobenzamide, timolol, tenoxicam, ketotifen, geldanamycin, dantrolene, dapsone, streptozocin, raloxifene, ambroxol, benzathine benzylpenicillin, finasteride, trifluoperazine, vanoxerine, thiamazole, homosalate, levomepromazine, co-dergocrine mesilate, oxyphenbutazone, promazine, carisoprodol, niclosamide, methoxamine, tocainide, cefotiam, maprotiline, resveratrol, and nadolol.

6. The method of claim 5, wherein the therapeutic composition comprises lansoprazole.

7. The method of claim 5, wherein the therapeutic composition comprises cefotaxime.

8. The method of claim 5, wherein the therapeutic composition comprises rifabutin.

9. The method of claim 5, wherein the therapeutic composition comprises chlortalidone.

10. The method of claim 5, wherein the therapeutic composition comprises benzathine benzylpenicillin.

11. The method of claim 5, wherein the therapeutic composition comprises maprotiline.

12. The method of claim 5, wherein the therapeutic composition comprises naproxen.

* * * * *